United States Patent

Young et al.

[11] Patent Number: 6,015,533
[45] Date of Patent: Jan. 18, 2000

[54] SENSOR HOUSING FOR A CALORIMETRIC GAS SENSOR

[75] Inventors: Daniel A. Young, Gurnee, Ill.; Neil J. Adams, Novi, Mich.; Armand Losinski, Albuquerque, N.Mex.

[73] Assignee: Motorola Inc., Schaumburg, Ill.

[21] Appl. No.: 08/970,698

[22] Filed: Nov. 14, 1997

[51] Int. Cl.[7] .................................................. G01N 7/00
[52] U.S. Cl. ........................... 422/83; 422/94; 422/95; 422/97; 422/98; 422/104; 204/428; 73/863.81; 73/864.33; 73/864.73; 73/864.81
[58] Field of Search ............................... 422/83, 94, 95, 422/97, 98, 104; 204/428; 73/864.33, 864.73, 864.81, 863.81

[56] References Cited

U.S. PATENT DOCUMENTS

| | | | |
|---|---|---|---|
| 3,835,012 | 9/1974 | Hemek | 204/195 S |
| 4,096,050 | 6/1978 | Kobayashi et al. | 204/195 S |
| 4,111,778 | 9/1978 | Davis et al. | 204/195 S |
| 4,141,813 | 2/1979 | Kita et al. | 204/428 |
| 4,339,318 | 7/1982 | Taneka et al. | 204/195 S |
| 4,466,880 | 8/1984 | Torri et al. | 204/428 |
| 4,507,192 | 3/1985 | Ebizawa et al. | 204/428 |
| 4,591,422 | 5/1986 | Kato et al. | 204/428 |
| 4,591,423 | 5/1986 | Kato et al. | 204/428 |
| 4,597,850 | 7/1986 | Takahasi et al. | 204/428 |
| 4,668,477 | 5/1987 | Nishio et al. | 204/428 |
| 4,897,174 | 1/1990 | Wang et al. | 204/425 |
| 4,905,652 | 3/1990 | Nakajima et al. | 123/479 |
| 4,927,517 | 5/1990 | Mizutani et al. | 204/406 |
| 4,929,331 | 5/1990 | Kato et al. | 204/428 |
| 5,177,464 | 1/1993 | Hamburg | 340/439 |
| 5,228,975 | 7/1993 | Yamada et al. | 204/424 |
| 5,238,552 | 8/1993 | Kato et al. | 204/428 |
| 5,250,169 | 10/1993 | Logothetis et al. | 204/424 |
| 5,265,417 | 11/1993 | Visser et al. | 60/274 |
| 5,324,415 | 6/1994 | Blumenthal et al. | 204/428 |
| 5,444,974 | 8/1995 | Beck et al. | 60/274 |
| 5,473,304 | 12/1995 | Friese et al. | 338/23 |
| 5,476,001 | 12/1995 | Hoetzel et al. | 73/23.31 |
| 5,505,073 | 4/1996 | Gerblinger et al. | 73/31.05 |
| 5,505,837 | 4/1996 | Friese et al. | 204/425 A |
| 5,689,059 | 11/1997 | Oh et al. | 73/23.31 |
| 5,707,504 | 1/1998 | Jyouno et al. | 204/428 |
| 5,711,863 | 1/1998 | Henkelmann et al. | 204/428 |
| 5,762,771 | 6/1998 | Yamada et al. | 204/428 |

FOREIGN PATENT DOCUMENTS

| | | |
|---|---|---|
| 259175 | 9/1987 | European Pat. Off. . |
| 704697 | 3/1996 | European Pat. Off. . |
| 704698 | 3/1996 | European Pat. Off. . |
| 0849587 A2 | 6/1998 | European Pat. Off. . |
| 0849588 A2 | 6/1998 | European Pat. Off. . |
| WO 97/33165 | 9/1997 | WIPO . |

OTHER PUBLICATIONS

U.S. application No. 08/650705, Koripella et al., filed May 20, 1996.

Primary Examiner—Randy Gulakowski
Assistant Examiner—S. Carrillo
Attorney, Agent, or Firm—Gary J. Cunningham

[57] ABSTRACT

A sensor housing (10) for directing the flow of a gas over two sensitive regions (53, 54) of sensing device (52) includes an inner shroud (12) surrounding the sensing device (52). The inner shroud (12) is inserted into an outer shroud (14), such that a plurality of gas channels (44) are formed between the inner shroud (12) and the outer shroud (14). In operation, a gas enters through inlet orifices (28) in the outer shroud (14) and travels through the gas channels (44) to the proximal end (26) of the inner shroud (12). The flow direction of the gas is then reversed and the gas passes through an inner chamber (50) and over sensitive regions (53), (54) located on the surface of the sensing device (52). Vacuum pressure created at an outlet hole (46) located at a distal end (35) of the outer shroud (14) draws the gas out of the inner chamber (50) and return the gas to the exterior of the sensor housing (10).

7 Claims, 4 Drawing Sheets

SENSOR HOUSING FOR A CALORIMETRIC GAS SENSOR

CROSS-REFERENCED TO RELATED APPLICATIONS

The present application is related to the following United States Patent Applications:

| Docket No. | Title | Serial No. | Filing Date |
|---|---|---|---|
| IR-4140e | Catalyst for Selective Oxidation of Hydrocarbons in HydrocarbonCarbon Monoxide Mixtures | 08/953,871 | Oct. 20, 1997 |
| IR-4189e | Catalyst Composition for Oxidizing Carbon Monoxide Selectively | 08/887,483 | Jul. 2, 1997 |
| IR-4313e | Unassigned Of Even Date | 08/970,944 | Nov. 14, 1997 |
| IR-4013e | Algorithm for Sensor Signal Processing for Automotive Catalytic Converter Evaluation | 08/903,524 | Jul. 30, 1997 |
| IR-4077e | Algorithm for Processing Oxygen Sensor Signals from on Board Diagnostics for Automobiles | 08/963,171 | Nov. 3, 1997 |
| IR-4077cipj | Algorithm for Processing Oxygen Sensor Signals from on Board Diagnostics for Automobiles | 08/970,946 | Nov. 14, 1997 |
| IR-4195e | Three Channel Pellistor Type Hydrocarbon Sensor | 08/970,940 | Nov. 14, 1997 |
| AP01701 | Calorimetric Hydrocarbon Gas Sensor | 08/970,837 | Nov. 14, 1997 |
| AP01733 | Method For Forming Porous Diffusion Barrier Layers | 08/970,486 | Nov. 14, 1997 |
| 300.002 | Exhaust Gas Sensor | 08/970,259 | Nov. 14, 1997 |
| 300.003 | Gas Sensor Having A Porous Diffusion Barrier Layer And Method Of Making Same | 08/970,672 | Nov. 14, 1997 |
| 300.004 | Exhaust Gas Sensor With Flow Control Without a Diffusion Barrier | 08/969,882 | Nov. 14, 1997 |
| 300.005 | Apparatus and Method for Determining Catalytic Converter Operation | 08/970,262 | Nov. 14, 1997 | the disclosures of which are hereby expressly incorporated herein by reference.

FIELD OF THE INVENTION

This invention relates, in general, to gas components sensors, and more particular, to hydrocarbon sensors having microcalorimeters in which a gas contacts a sensitive region.

BACKGROUND OF THE INVENTION

Sensors for the detection of particular compounds present in a high temperature gas stream find numerous applications in many different mechanical systems. For example, detection of certain compounds in a high temperature gas stream is important in industrial emission monitoring for detection of gas pollutants, such as sulfur dioxide ($SO_2$), in residential heating systems for detection of carbon monoxide (CO), and in automobile exhaust systems for various compounds including hydrocarbons.

In automotive applications, gas sensors can be placed at various locations in an exhaust system. Exhaust gas from an internal combustion engine typically contains hydrogen ($H_2$), carbon monoxide (CO), methane ($CH_4$), carbon dioxide ($CO_2$), oxides of nitrogen ($NO_x$), water ($H_2O$), and non-methane hydrocarbons ($C_nH_m$), where n is an integer larger than 1 and m is an integer whose value depends upon the kind of hydrocarbon compound, for example, alkane, alkene, alkyl, or aryl. Important environmental pollution concerns dictate that the emission of hydrocarbons be minimized. To minimize pollutants in the engine exhaust, sensors can be placed before and after the catalytic converter to monitor the performance of the converter. Also, the emission of hydrocarbons can be controlled, in part, by an engine exhaust control system that receives a feedback signal from an exhaust sensor capable of selectively detecting the presence of hydrocarbons in the engine exhaust.

Several types of sensing elements have been developed for detecting various chemical species within a gas stream. These sensing elements includes calorimetric sensors having a catalyst coating, or a semiconductor metal oxide, or the like. Calorimetric hydrocarbon gas sensors measure the amount of heat released by the catalytic oxidation of hydrocarbons contained within the exhaust gas. To obtain optimum sensitivity for the measurement of hydrocarbon species within a gas stream, a calorimetric hydrocarbon gas sensor must be designed to maintain a relatively constant internal temperature, and the flow of gas within the sensor must be carefully regulated. This requirement is especially important given the wide temperature variations encountered in an industrial or automotive gas system.

In addition to temperature regulation requirements, precise gas concentration measurements require that a reference catalyst be provided in close proximity to a measurement catalyst. The reference catalyst is used to compensate for environmentally induced temperature responses in the microcalorimeters, and to provide a means for selectively measuring the concentration of one particular chemical species within the gas stream. In order for the dual catalyst system to function properly, the gas flow conditions must be identically maintained in regions proximate to each catalyst. This requires that the temperature, flow velocity, and turbulence conditions of the gas in proximity to each catalyst be substantially the same. The maintenance of precisely controlled gas flows within a gas sensor becomes especially important when the sensor is deployed within a high velocity gas stream, such as an automotive exhaust system, or an industrial gas expulsion system, or the like. Accordingly, a need existed for an apparatus capable of precisely regulating the temperature and flow conditions of a gas within a gas sensor.

Figure 1:
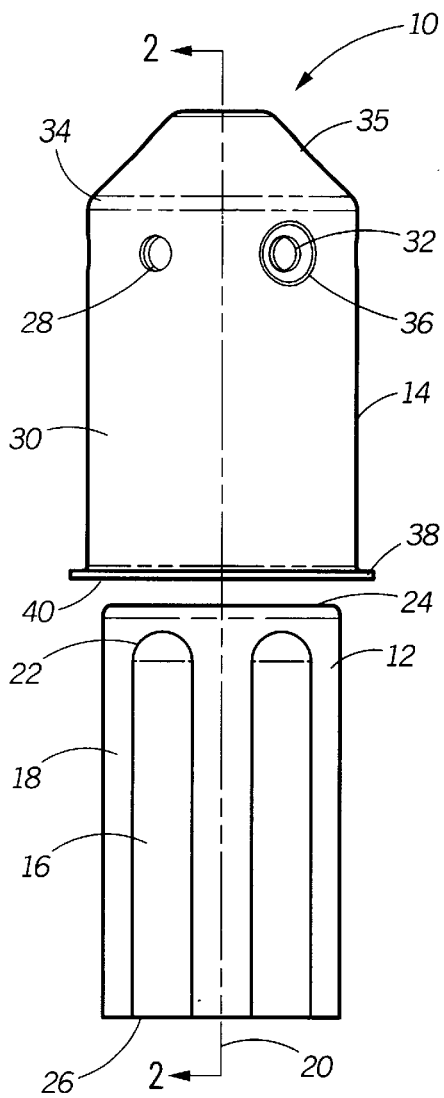
FIG. 1 illustrates a cross sectional assembly view of a sensor housing configured in accordance with one embodiment of the invention.

It will be appreciated that for simplicity and clarity of illustration, elements shown in the Figures have not necessarily been drawn to scale. For example, the dimensions of some of the elements are exaggerated relative to each other. Further, where considered appropriate, reference numerals have been repeated among the Figures to indicate corresponding elements.

DETAILED DESCRIPTION OF PREFERRED EMBODIMENTS

The present invention is for a sensor housing including a shroud assembly that functions to protect a sensing device within a calorimetric gas sensor, and to control gas flow from a rapidly moving gas stream to the sensing device. The sensing device that is housed within the shroud assembly includes two or more separate microcalorimeters. For precise measurements, each microcalorimeter must be exposed to identical quantities of gas having the same temperature, composition and flow rate. Proper functioning of the calorimetric gas sensor depends upon the ability of the sensor housing to channel gas from a rapidly moving gas stream into the sensor and over each microcalorimeter without introducing a difference in the thermal or chemical composition of the gas contacting each calorimeter. The sensor housing must reduce the gas velocity in order to limit the magnitude and the variability of the heat exchanged between the gas and the calorimeters. Additionally, the gas velocity must be reduced to limit the gas component measurement variability associated with flow velocity.

As a practical matter, it is impossible for the sensor housing not to affect the composition of the gas to some slight extent. However, the important aspect of proper gas sensor function depends upon the ability of the sensor housing to ensure that each microcalorimeter is exposed to gas that has equal composition and minimal turbulence.

In addition to the meeting the gas handling requirements, the sensor housing of the invention is also designed to couple with an electrical cable harness for the electrical connection of the sensing device within the sensor housing. Accordingly, the sensor housing of the invention functions to expose each microcalorimeter to separate, identical gas flows by directing the gas flows along a main axis of the gas sensor. Additionally, the sensor housing of the invention maintains equal thermal environments, and provides similar gas flow velocity profiles along respective surfaces of each microcalorimeter.

FIG. 1 illustrates, an assembly view of a sensor housing 10 in accordance with a preferred embodiment of the invention. Sensor housing 10 includes an inner shroud 12 inserted within an outer shroud 14. Each shroud is a tube like assembly that can be slidably mounted over a sensing device and couple with a cable harness. Inner shroud 12 contains a plurality of flutes 16 machined into an outer surface 18. Each of flutes 16 extends along exterior surface 18 parallel to a major longitudinal axis 20. Additionally, each of flutes 16 has a rounded end 22 in proximity to a distal end 24 of inner shroud 12. Flutes 16 terminate at a proximal end 26 of inner shroud 12.

Outer shroud 14 includes a plurality of inlet orifices 28. Inlet orifices extend from an exterior surface 30 to an interior surface 32 of outer shroud 14. In the embodiment illustrated in FIG. 1, inlet orifices 28 are arranged around outer shroud 14 in proximity to a circular bend 34 located at distal end 35. Selected ones of inlet orifice 28 are slightly recessed in exterior surface 32 of outer shroud 14 to form recessed orifices 36. Recessed orifices 36 have a gradually tapered diameter starting at exterior surface 30 and extending to interior surface 32.

Figure 2:
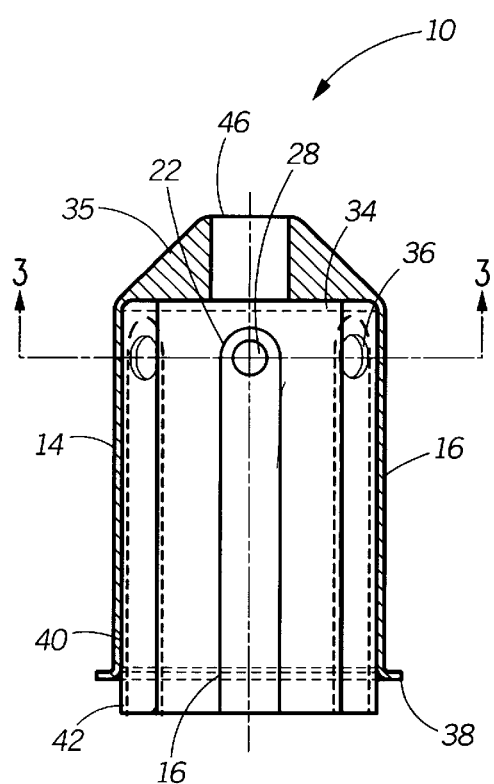
FIG. 2 illustrates an assembled view of the sensor housing shown in FIG. 1.

A longitudinal cross section of sensor housing 10 taken along section line 2—2 is shown in FIG. 2. When inserted into outer shroud 14, distal end 24 of inner shroud 12 engages bend 34 in outer shroud 14 and proximal end 26 protrudes past a flange 38 located at a proximal end 40 of outer shroud 14. Each of flutes 16 is aligned with one of inlet orifices 28, such that each rounded end 22 resides near one of inlet orifices 28. Further, at least one of recessed orifices 36 engages a selected one of flutes 16 near rounded end 22 to prevent the axial rotation of inner shroud 12 against outer shroud 14. Upon insertion of inner shroud 12 into outer shroud 14, a portion 42 of inner shroud 12 protrudes below flange 38.

Figure 3:
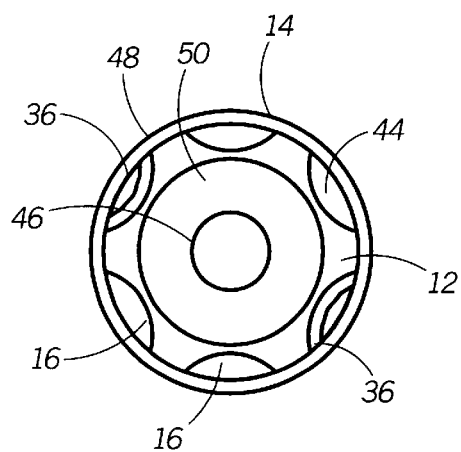
FIG. 3 illustrates a cross sectional view of the sensor housing shown in FIG. 2 taken along section line 3—3.

FIG. 3 illustrates a cross sectional view of sensor housing 10 taken along section line 3—3 of FIG. 2. The coupling of inner shroud 12 with outer shroud 14 and the alignment of flutes 16 with inlet orifices 28 produces a plurality of gas channels 44 positioned around the perimeter of shroud assembly 10. As previously described, the interlocking feature of recessed orifices 36 and associated flutes 16 prevents the differential rotation of inner shroud 12 against outer shroud 14. In addition to the resistance to differential rotation provided by recessed orifices 36, a tack weld 48 can be used to further secure inner shroud 12 within outer shroud 14. An outlet opening 46 is positioned at the apex of distal end 35 of outer shroud 14. A chamber 50 resides within inner shroud 12 and communicates with regions external to sensor housing 10 through outlet opening 46.

Figure 4:
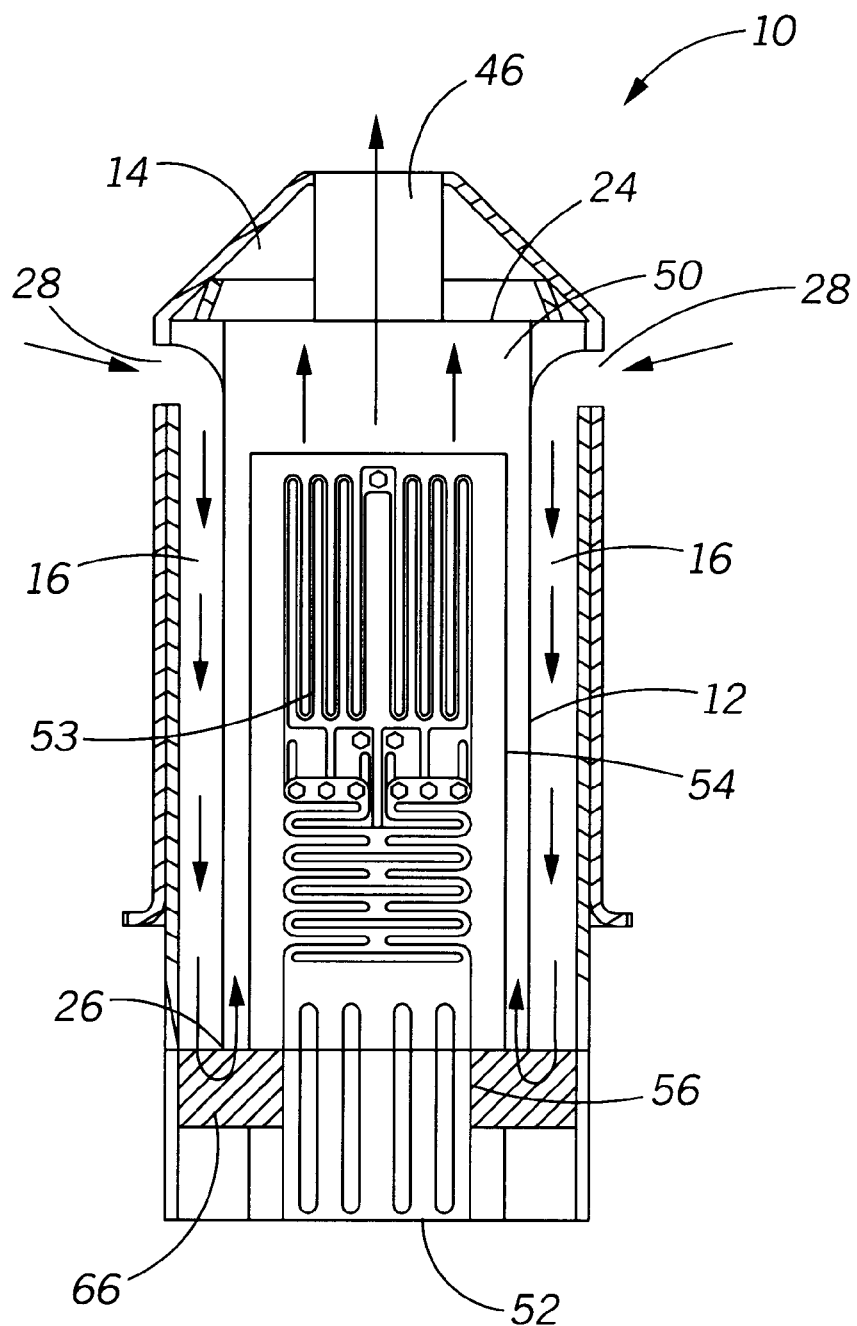
FIG. 4 illustrates, a cross sectional view of a sensor housing having a sensing device inserted therein.

FIG. 4 illustrates a sectional view of sensor housing 10 having a sensing device 52 positioned within chamber 50. FIG. 4 further illustrates the flow of a gas through inlet orifices 28 and into flutes 16. The gas travels through flutes 16 towards proximal end 26 of inner shroud 12. At proximal end 26, the gas diffuses into a fibrous material layer 66. Then, in response to a vacuum created at outlet opening 46, the gas reverses direction and proceeds toward distal end 24 of inner shroud 12. Fibrous material layer 66 disrupts uneven flow patterns in the gas, such as swirling, and causes the gas flow through inner shroud 12 to be more nearly uniform. As the gas travels from proximal end 26 to the distal end 24, the gas passes over two sensitive regions 53 and 54 that are disposed on an upper surface of sensing device 52. Sensitive regions 53 and 54 are components of two microcalorimeters located within sensing device 52. Each sensitive region includes a catalyst material that selectively catalyzes the oxidation of certain chemical species within the gas.

After passing over sensitive regions 53 and 54, the gas is drawn out of chamber 50 through outlet opening 46. As illustrated in FIG. 4, by aligning flutes 16 with inlet orifices 28, outer shroud 14 cooperates with inner shroud 12 to direct the gas from regions external to sensor housing 10 through the gas channels 44 created by flute 16 to proximal end 56 of sensing device 52. Preferably, as the gas passes through gas channels 44 and into chamber 50, a velocity reduction occurs and the flow changes from turbulent flow to substantially laminar flow. Subsequently, a vacuum created at outlet opening 46 directs the gas, now at laminar flow, from proximal end 56 through chamber 50 and through outlet opening 46.

Those skilled in the art will recognize that sensor housing 10 can be employed for a variety of gas transfer operations.

For example, the arrangement of orifices and annular spaces created by coupling inner shroud 12 and outer shroud 14 permits samples to be taken from a rapidly moving, turbulent gas stream. The gas samples taken from the gas stream are transformed to a uniform laminar flow and transported past a composition measuring device. Accordingly, the shroud assembly of the invention can be used with a variety of gas sensing devices that require a uniform gas flow for precision gas component measurement.

Figure 5:
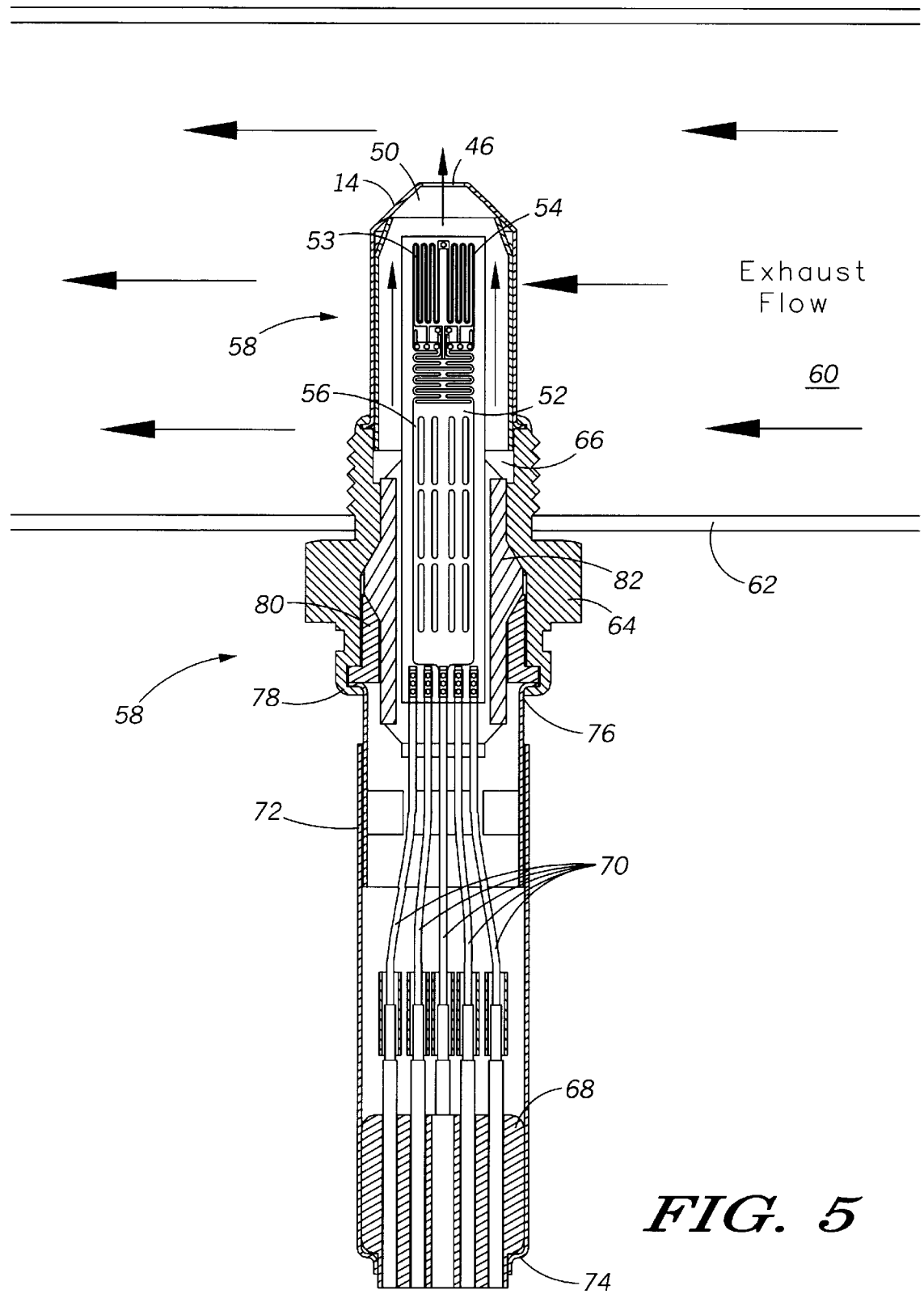
FIG. 5 illustrates a cross sectional view of a calorimetric gas sensor having a sensor housing inserted into a gas stream.

FIG. 5 illustrates a cross sectional view of a calorimetric gas sensor 58 inserted into a gas stream 60. Gas sensor 58 is attached to a wall 62 by a threaded housing 64. An electrical cable harness 68 supports electric cables 70 and is attached to a coupling 72. Coupling 72 is configured at a first end 74 to engage electrical cable harness 68, and configured at a second end 76 to engage a flange 78 on threaded housing 64. A seal 80 surrounds a lower portion of a bracket 82 and engages the lower portion of threaded housing 64.

Seal 80 prevents the gas entering calorimetric gas sensor 58 through sensor housing 10 from escaping chamber 50 at proximal end 56 of sensing device 52 and flowing into coupling 72. As denoted by the arrows in FIG. 5, gas flowing in gas stream 60 is directed past sensitive regions 53 and 54 and is returned to gas stream 60 through outlet opening 46. It is important to note that the gas flow management provided by sensor housing 10 causes a portion of the gas from rapidly moving gas stream 60 to be channeled in a uniform manner past sensitive regions 53 and 54 in a direction orthogonal to the flow of gas stream 60. Thus, the apparatus of the invention enables gas laterally impinging upon calorimetric gas sensor 58 to be orthogonally transferred in a uniform manner past sensitive regions 53 and 54 in such a way that the sensitive regions can precisely measure the various components within gas stream 60.

Figure 6:
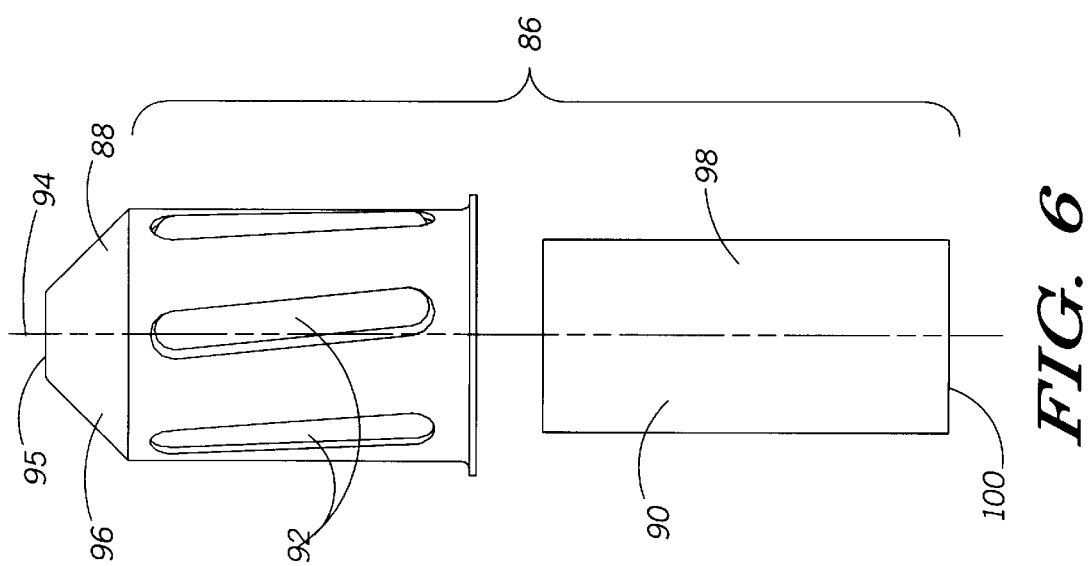
FIG. 6 is a cross sectional assembly view of a sensor housing configured in accordance with a second embodiment of the invention.

FIG. 6 illustrates a cross sectional assembly view of a sensor housing configured in accordance with a second embodiment of the invention. A sensor housing 86 includes an outer shroud 88 and an inner shroud 90. Outer shroud 88 has a plurality of elongated slots 92 that are rotated about a central longitudinal axis 94. Slots 92 extend from an exterior surface to an interior surface of outer shroud 88. Outer shroud 88 further includes an exit hole 95 located at the apex of a distal end 96 of outer shroud 88. Inner shroud 90 is an elongated tube structure having a smooth exterior wall surface 98. In a manner similar to the previous embodiment, inner shroud 90 is inserted into outer shroud 88, such that a gas passage way is formed between outer shroud 88 and inner shroud 90. In operation, gas enters slots 92 and travels along smooth wall surface 98 to a proximal end 100 of inner shroud 90.

Figure 7:
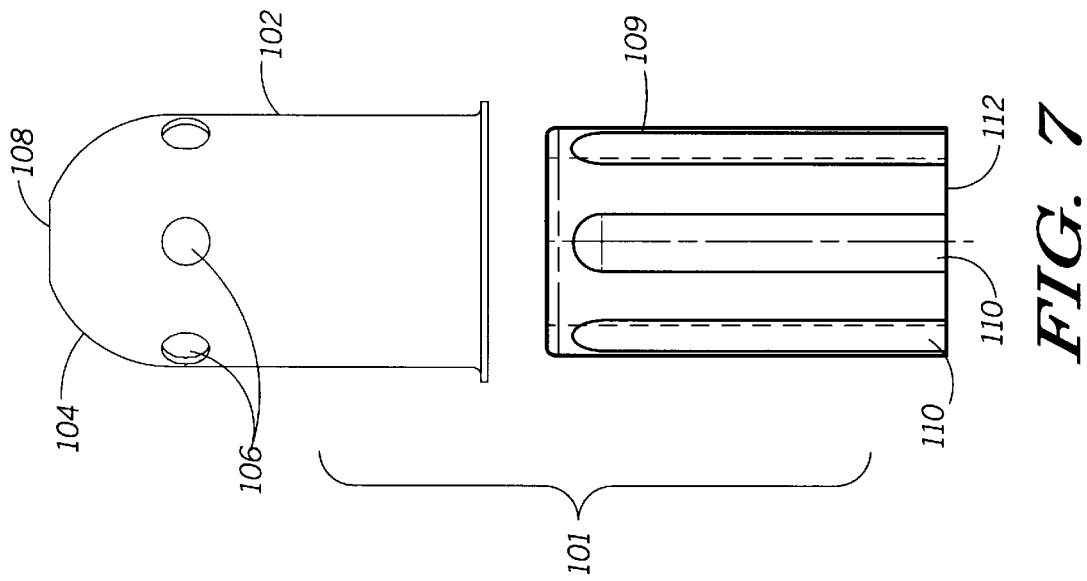
FIG. 7 illustrates a cross sectional assembly view of a sensor housing configured in accordance with a third embodiment of the invention.

Yet another embodiment of the invention is illustrated in the cross-sectional assembly view of FIG. 7. An outer shroud 102 has a rounded distal end 104, and a plurality of inlet orifices 106 are arrayed around the perimeter of outer shroud 102. An exit hole 108 is located at the apex of rounded distal end 104. An inner shroud 109 has a plurality of flutes 110 arranged around an exterior surface. In a manner similar to the embodiment illustrated in FIG. 1, inner shroud 108 is inserted into outer shroud 102, such that each of flutes 110 is aligned with one of inlet orifices 106. The alignment of the flutes and the inlet orifices creates a plurality of gas channels, whereby gas entering inlet orifices 106 is transmitted to a proximal end 112 of inner shroud 109.

As previously described, gas exits the sensor housing through the outlet hole located at the apex of the distal end of the outer shroud. A rapidly moving gas stream passing at right angles to the outer shroud creates a low pressure region at the exit hole relative to the pressure inside the shroud assembly. Those skilled in the art will appreciate that the surface geometry of the outer shroud can influence the pressure difference across the exit hole. The specific shape of the distal end of the outer shroud can influence the velocity of the gas passing the exit hole. The higher the orthogonal gas velocity, the greater the pressure difference across the exit hole. Accordingly, the use of a variety of geometric configurations near the exit hole it is contemplated by the present invention. For example, FIGS. 1 and 6 illustrate outer shrouds having a tapered end profile, while FIG. 7 illustrates an outer shroud having a rounded end profile. Depending upon the amount of vacuum pressure needed at the exit hole, other end profiles can be formed. For example, a concave profile in which the distal end is inverted with respect to the side walls, and a flat edge end profile, and the like, could also be formed in the outer shroud.

Thus it is apparent that there has been provided, in accordance with the invention, a sensor housing for a calorimetric gas sensor that fully meets the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. For example, many different types of sensing devices can be used within the sensor housing, such as a heated-exhaust-gas-sensor (HEGO), a universal-exhaust-gas-sensor (UEGO), a nitrogen oxide ($NO_x$)sensor, and the like. It is therefore intended to include within the invention all such variations and modifications as fall within the scope of the appended claims and equivalents thereof.

We claim:

1. A sensor housing for directing flow of a gas from an external gas stream over a sensing device comprising:

an outer tube longitudinally extending about an axis and having an interior surface and an exterior surface and having a first end opposite a second end;

an inner tube insertably mounted within the outer tube and longitudinally extending about the axis, the inner tube having an interior surface and an exterior surface and having a first end opposite a second end;

a sensing device positioned within the inner tube; a coupling structure closing the first end of the outer tube and the first end of the inner tube to gas flow;

a plurality of flutes on the exterior surface of the inner tube; and a plurality of inlet orifices in the outer tube extending from the interior surface of the outer tube to the exterior surface of the outer tube and an outlet orifice at the second end of the outer tube extending from the interior surface of the outer tube to the exterior surface of the outer tube, wherein each of the plurality of flutes on the exterior surface of the inner tube is arranged in spaced relationship with one or more of the plurality of inlet orifices in the outer tube, wherein the outlet orifice at the second end of the outer tube communicates with the sensing device, and wherein a recessed region of the interior and exterior surface of the outer tube surrounds selected ones of the plurality of inlet orifices in the outer tube, such that the recessed regions engage selected ones of the plurality of flutes in the exterior surface of the inner tube.

2. The sensor housing of claim 1, wherein the coupling structure comprises:
- a coupling having a first end configured to engage an electrical cable harness and a second end having a coupling flange;
- an outer housing having a first end configured to engage the first end of the outer tube and a second end configured to engage the coupling flange;
- a bracket positioned within the outer housing;
- a seal surrounding a portion of the bracket and pressed against the outer housing preventing the transmission of gas therethrough.

3. The sensor housing of claim 1, wherein the plurality of inlet orifices and the plurality of flutes cooperate to channel the flow of gas in a direction parallel to the axis toward the first end of the inner tube, and wherein the outlet orifice cooperates with the external gas stream to produce a vacuum at the outlet orifice, such that the flow of gas is directed.

4. A sensor housing for directing flow of a gas from an external gas stream over a sensing device comprising:
- a sensing device having a first end opposite a second end;
- a sensitive region disposed on the second end of the sensing device;
- an inner shroud surrounding the sensing device; and
- an outer shroud surrounding the inner shroud and defining an annular space therebetween, wherein the outer shroud has a rounded apex and a gas outlet opening at the apex, and
- wherein recessed orifices in the outer shroud engage flutes on the inner shroud to direct the flow of gas from the external gas stream through the annular space to the first end of the sensing device and to direct the flow of gas from the first end of the sensing device to the sensitive region, and to return the flow of gas to the extend gas stream through the gas outlet opening.

5. The sensor housing of claim 4, wherein the inner shroud comprises an elongated tube having an exterior surface and a plurality of flutes on the exterior surface, and wherein the outer shroud comprises an elongated tube having a plurality of orifices extending from an exterior surface to an interior surface thereof, and wherein the gas outlet opening is located in a distal end of the outer shroud and is located proximate to the second end of the sensing device.

6. The sensor housing of claim 5, wherein the flutes comprise elongated parallel rounded grooves in the exterior surface of the inner shroud.

7. The sensor housing of claim 5, wherein the outer shroud further comprises a proximal end closed to gas flow by an end connector, and wherein the distal end is rounded, and wherein the gas outlet opening is located at an apex of the distal end.

* * * * *

UNITED STATES PATENT AND TRADEMARK OFFICE
CERTIFICATE OF CORRECTION

PATENT NO. : 6,015,533
DATED : January 18, 2000
INVENTOR(S) : Daniel A. Young; Neil J. Adams; Armand Losinski It is certified that error appears in the above-identified patent and that said Letters Patent is hereby corrected as shown below:

Column 7, line 16, after "orifice" insert --at the second end of the outer tube--

Column 7, line 18, after "directed" insert --towards the second end of the inner tube to the sensing device, wherein the flow of gas exits the sensor housing through said outlet orifice of the outer tube--

Column 8, line 7, delete "extend" and substitute --external-- therefore.

Signed and Sealed this

First Day of May, 2001

*Attest:*

NICHOLAS P. GODICI

*Attesting Officer*   *Acting Director of the United States Patent and Trademark Office*